United States Patent [19]

Nelvig

[11] Patent Number: 6,002,742
[45] Date of Patent: Dec. 14, 1999

[54] METHOD AND DEVICE FOR TRIGGERING OF X-RAY IMAGE SENSOR

[75] Inventor: Per Nelvig, Sundsvall, Sweden

[73] Assignee: AFP Imaging Corporation, Elmsford, N.Y.

[21] Appl. No.: 08/157,028

[22] PCT Filed: Jan. 6, 1992

[86] PCT No.: PCT/SE92/00369

§ 371 Date: Dec. 1, 1993

§ 102(e) Date: Dec. 1, 1993

[87] PCT Pub. No.: WO92/22188

PCT Pub. Date: Dec. 10, 1992

[30] Foreign Application Priority Data

Jun. 3, 1991 [SE] Sweden ................................. 9101682
Jun. 1, 1992 [WO] WIPO ..................... PCT/SE92/00369

[51] Int. Cl.⁶ ........................................................ H05G 1/64
[52] U.S. Cl. ........................................ 378/98.8; 378/210
[58] Field of Search ............................................ 378/98.8

[56] References Cited

U.S. PATENT DOCUMENTS

| | | | |
|---|---|---|---|
| 4,035,650 | 7/1977 | Franke | 378/197 |
| 4,628,356 | 12/1986 | Spillman et al. | 378/98.8 |
| 4,901,336 | 2/1990 | Nishiki . | |
| 4,901,337 | 2/1990 | Fujimoto | 378/98.8 |
| 4,905,265 | 2/1990 | Cox et al. . | |
| 5,101,421 | 3/1992 | Nishiki | 378/98.8 |

FOREIGN PATENT DOCUMENTS 0 415075 A1  3/1991  European Pat. Off. .

*Primary Examiner*—Craig E. Church
*Attorney, Agent, or Firm*—Cooper & Dunham LLP

[57] ABSTRACT

The present invention demonstrates a method and a device in the technique of using an image sensing member, preferably a CCD cell instead of a film sensitive to X-ray radiation. The method and the device is applicable to a general X-ray arrangement without any necessary direct connection between the image sensing member and the X-ray arrangement. A number of detector points for X-ray radiation are provided at or in the CCD cell. The method and device of the present invention result in minimizing of the radiation dose to exactly that which is needed for exact imaging exposure of an image, and therefore more images may be obtained within the same total normal radiation dose.

14 Claims, 2 Drawing Sheets

METHOD AND DEVICE FOR TRIGGERING OF X-RAY IMAGE SENSOR

TECHNICAL FIELD

The present invention relates to an improved method of triggering and an improved arrangement of X-ray detection at an image sensor for electronically producing X-ray images, and more specifically a method and an arrangement which except for true triggering of the image sensor also limits the X-ray radiation dose when using a type CCD X-ray imaging cell. A simple direct control of the X-ray apparatus is also provided.

BACKGROUND OF THE INVENTION

X-ray examinations normally have been conducted by putting the examined organ between an X-ray sensitive film and an X-ray source and radiating X-rays. Film exposed in this way being developed in a normal manner, will show different blackening dependent upon the type and amount of tissue between the X-ray source and the film.

The method among other things has a drawback in that it is not simply reproducible. Images made during what may seem to be the same conditions may present very different blackening and resolution of the interesting areas of the organ being examined. Further the method is labor and time consuming as the result is achieved only after developing of the film.

Within the field of dental X-raying there is now also an application using for example a CCD cell similar to that in an ordinary video camera. This CCD cell is put instead of the X-ray sensitive film in an appropriate manner in the oral cavity of a patient behind the tooth or teeth to be examined, whereby an image direct from the CCD cell may be achieved on a display by means of known technique in the art by using an electronic interface and an ordinary PC computer. This has the advantage that the result is immediately obtained and if this image is not adequate a new exposure may be immediately performed.

In this technique the control electronics of the CCD cell itself has an electrical connection to the X-ray apparatus, such that the electronic interface receives information when the X-ray radiation is activated. This implies that such an arrangement has to particularly be adopted to each available type of X-ray equipment to implement this type of synchronization.

When X-ray images are produced by an image sensing member in the shape of a CCD cell at existing temperatures, e.g. in the oral cavity, dark currents exists which all the time are adding up charges within the CCD cell. These charges are added up so fast that the image sensing member will normally be saturated after one or a few seconds. Therefore, the CCD cell must be emptied of charges before the exposure by X-rays is started. When the X-ray image is fully exposed it must immediately be read out in its totality in order not to loose image information due to the adding of dark currents.

Such a synchronization may be achieved by either activating the X-ray tube short before the scanning is started of for example the CCD cell or initiating scanning from the X-ray arrangement, eventually with a delay such that the radiation source comes to full power. In both cases there is a general demand of considerable interfacing equipment to achieve this. Otherwise the exposure time of the X-ray source must be chosen unnecessarily long to ensure a good result.

According to the state of the art it is not unusual to willingly overexpose a bit to be certain of an acceptable result of the X-ray examination. One problem which then additionally has to be solved is that the accumulated radiation dose of the patient has to be optimized in order to minimize the radiation dose to the patient, which is utterly important from the general standpoint of radiation protection.

A radiation sensor for dental X-ray examination is known from the German utility model G 89 09 398.4.(EP-A1-0 415 075). The imaging device then has a single radiation detector, placed in front of, at the side of or behind the imaging device. The single radiation detector as such may comprise one or more phototransistors having a scintillation layer. One drawback in such an arrangement is that the single radiation detector may be shaded by, for example bone or a tooth when the imaging device is placed into the oral cavity of a patient and thus will detect very little radiation as bone or a tooth will still be very opaque to the kind of X-ray radiation used for dental examination. Additionally the device uses only remote electronics for processing the obtained signals which gives a low efficiency for utilizing the small current generated in the scintillation layer of the radiation sensor.

DESCRIPTION OF THE INVENTION

The invention is based on the technical possibility by means of a simple control equipment to deactivate the source of radiation after it is started, by a method of detecting radiation using several sensing diodes at the back of a CCD device or the multitude of charging pixel capacitors within the CCD device. Triggering may be effected when the radiation source is activated and a measure has been obtained that a sufficient radiation dose producing the desired imaging.

A first object of the present invention therefore is to teach a method and apparatus which do not demand a complex interfacing to each individual X-ray equipment e.g. for dental X-ray, the technique using preferably a CCD cell, a direct connection between the image sensing and the X-ray apparatus normally not being needed.

A second object of the present invention is to teach a method apparatus which improve adaption of the exposure of the X-ray image at the image sensing member such that scanning of the image immediately starts when sufficient exposure reliably has been detected or immediately as the radiation of X-rays ceases.

A third object of the present invention is to teach a method and apparatus implying that the radiation dose is minimized to exactly what is needed to satisfactorily expose an image by using a signal from the arrangement to deactivate the X-ray apparatus, implying according to the present invention that more images may be obtained within the same total normal radiation dose.

Another object of the present invention is to provide an improved method and apparatus for the X-ray image sensor by an arrangement wherein the X-ray radiation is activated and deactivated by sensing X-ray radiation by using several detection points to thereby measure the overall dose.

A further object of the invention is to optimize the exposure by sensing the total radiation dose and initiating the scanning out of image data from the image sensing member when sufficient exposure has been obtained.

Another object of the present invention is to provide an apparatus and method which minimizes the radiation dose to the patient in connection with an X-ray examination by producing an external signal which in turn may be used for the control of the deactivation of the X-ray apparatus.

DESCRIPTION OF THE DRAWINGS

The present invention will be described in a preferred embodiment by means of the attached drawings in which FIG. 1 demonstrates a cross-section in part of the encapsuled image sensing arrangement of a preferred embodiment, FIG. 2a demonstrates the image sensing member of the encapsuled arrangement from above, FIG. 2b demonstrates the rear side of the image sensing member of FIG. 2a, FIG. 2c demonstrates the front side of the image sensing member of FIG. 2a, and FIG. 3 demonstrates a diagram of the electronic circuitry of interfacing units according to the invention.

A PREFERRED EMBODIMENT

Figure 1:
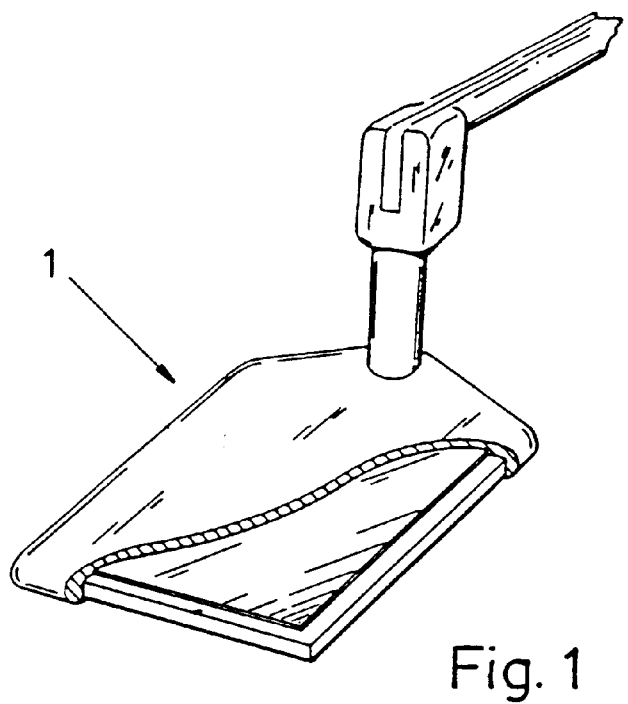
Figure 2A:
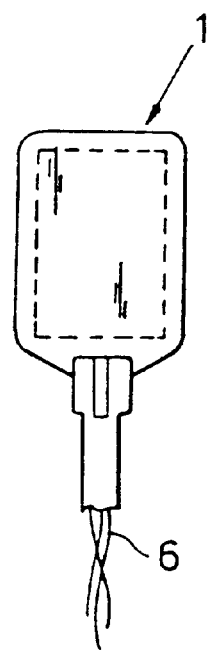

In FIG. 1 is demonstrated a preferred embodiment for dental X-ray of an arrangement 1 to be inserted into the mouth of a patient. The arrangement in the preferred embodiment comprises a CCD cell supplied and controlled by lines 6 seen in FIG. 2a. For dental X-ray the arrangement 1 is positioned such that the specific tooth or teeth is/are between the front side (upper side in FIG. 1) of the arrangement 1 and an X-ray radiation source. The CCD cell of the arrangement 1 then will be exposed differently dependent upon the opacity for X-ray radiation of the tooth or teeth and thereby an X-ray image of the tooth or teeth is obtained in the CCD cell according to the state of the art.

Figure 2B:
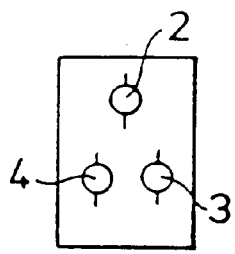
Figure 2C:
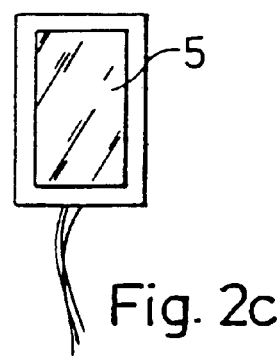

FIG. 2c demonstrates the side having an image sensing member 5, for example, in the form of a CCD cell lying on a base formed by a substrate or a printed circuit board, whereby the member 5 is turned towards the tooth or teeth during the X-ray examination. In FIG. 2b the rear side of the substrate or printed circuit board is shown, on which in the preferred embodiment three sensor elements 2, 3 and 4 are scattered over the surface. The sensor elements constitute detector diodes having a scintillation portion and are in the preferred embodiment of type BPW 34 produced by Telefunken. It is essential that these detector diodes 2, 3 and 4 are placed such that they do not hide any portion of the image surface and are within the area of the maximum radiation dose. Therefore the detector diodes are preferably spread on the rear side of the image sensing member. Consequently the number of detector diodes must be more than two to ensure that at least one diode may be put into a position where it will be accessed by not too much reduced X-ray radiation. In a first embodiment shown there are at least three detector diodes 2, 3 and 4 connected in parallel. In another embodiment of the invention the CCD cell itself is used also as the sensor of X-ray radiation. The CCD cell includes a large number of individual storage capacitors formed on the semiconductor substrate and these individual capacitors will be charged due to the incident photons of the X-ray radiation. When these capacitors are charged a certain amount of current will flow to or from the CCD device, which integrated current when exceeding a certain threshold will be used as a detection criteria.

Figure 3:
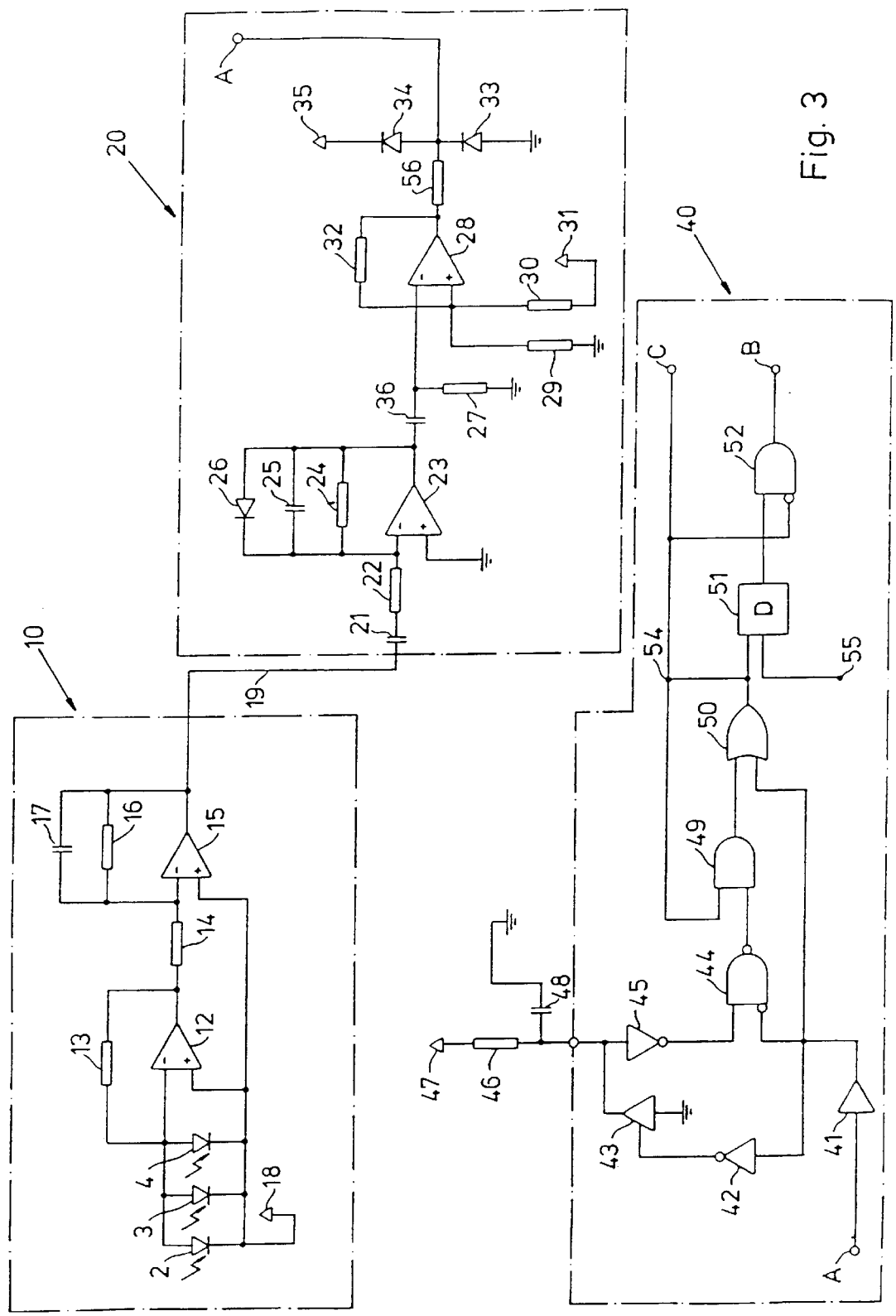

In FIG. 3 is shown an electronic circuitry indicating the connection of the detector diodes to an interfacing electronic unit in the preferred embodiment consisting of two portions 10 and 20. The interfacing electronic unit portion 10 is integrated together with the detector diodes 2, 3 and 4 at the rear side of the image sensing member 5 of the preferred embodiment, while the other portion is found in an external electronic unit (not shown) and connected to the portion 10 by the connecting lines 6. Instead of the signal from the detector diodes 2, 3 and 4 the charging current signal from the CCD device is used in the other preferred embodiment of the invention and connected to the input of the electronic unit 10.

The interfacing unit portion 10 also comprises two operational amplifiers 12 and 15, resistors 13, 14 and 16 and a capacitor 17. Further the cathode side of the detector diodes are connected to signal ground via a point 18. The operational amplifiers of the preferred embodiment is of type TL072 produced by Texas Instruments Corporation.

The interfacing unit portion 20 also comprises two operational amplifiers 23 and 28 and resistors 22, 24, 27, 29, 30, 32 and 56 and capacitors 21, 25 and 36. Additionally the resistor 30 is connected to −12 V at a point 31. The interfacing unit 20 further comprises three semiconductor diodes 26, 33 and 34. Additionally the interfacing unit portion 20 has a signal output A. The operational amplifiers 23 and 28 of the preferred embodiment are of type TL072 produced by Texas Instruments Corporation while the diodes 26, 33 and 34 are of type BAS16 produced by Philips.

From the interfacing unit portion 20 signals go to an additional electronic unit in the form of a logic device generally denoted 40 only a small portion of which is shown. The logic device 40 is of type XC3030-44, produced by XILINK, San Jose, Calif. The logic device also comprises a read and write memory in the shape of a RAM, in which, for example, any user program may be loaded to define the different logic functions obtained by this circuit. Such functions include for example, clocking of the CCD cell when reading out image data, which does not constitute a part of the invention as such but is known by a person skilled in the art. The demonstrated portion of the logic device 40 has one input A and two outputs B and C. The portion of the logic device 40 shown in FIG. 3 comprises buffers 41, 42, 43 and 45, the buffers 42 and 45 having an inverted output. The buffer 43 is a three state output buffer, having high, low and floating states. The high and the low states, respectively, correspond as usual to logic one and logic zero, respectively. Additionally there are AND gates 44, 49 and 52 having two inputs, where AND gate 44 and 52 each are provided with an inverted input and the AND gate 44 additionally also has an inverted output. The portion of the logic device 40 shown further comprises an OR gate 50 and a D-type flip-flop circuit 51. The D-type flip-flop circuit is also provided with a clocking input 55. The buffers 41, 42, 43, 45 and the gates 44, 49, 50 together form a monostable circuit which is triggered from the input A. The time constant of the monostable circuit is set forth by the resistor 46 and the capacitor 48.

In the table below is given the values of the resistors and capacitors shown in the circuit diagram of the preferred embodiment of FIG. 3.

| Resistor | | Capacitor | |
| --- | --- | --- | --- |
| 13 | 10M | 17 | 330 pF |
| 14 | 100K | 21 | 10 µF |
| 16 | 1M | 25 | 1,5 nF |
| 22, 29 | 220K | 36 | 1 µF |
| 30 | 820K | 48 | 47 nF |
| 24 | 2,2M | | |
| 27 | 2,7M | | |

-continued

| Resistor | Capacitor |
|---|---|
| 32 | 1,8M |
| 46 | 560M |
| 56 | 150R |

In brief the function of the circuitry is as follows. When any of the sensor elements 2, 3 and 4 is subject to X-ray radiation it will produce current which is fed into the input of the first operational amplifier 12. Similarly, when the CD device is subject to an X-ray radiation it will produce a current due to the charging of the individual capacitors constituting the individual pixel elements, which current alternatively is fed to the first operational amplifier. This amplifier 12 through resistor 13 serves as a current to voltage converter. The voltage signal from the output of operational amplifier 12 is carried via resistor 14 to the input of amplifier 15, which will amplify the signals from the sensor elements normally being pulses having the line frequency, e.g. 50 Hz, the X-ray tube being supplied with such a pulsating high tension. Capacitor 17 together with resistor 16 acts as a filter to, for example, eliminate unwanted spikes but still preserves the amplified voltage pulses from amplifier 12. Amplifiers 12 and 15 in the preferred embodiment are situated at the substrate or on the circuit board at the rear side of the image sensing member together with the three sensor elements 2, 3 and 4 and thus constitute the interfacing unit portion 10.

From the electronic unit constituting the interfacing unit portion 10 the output signal is carried from amplifier 15 to the input of the interfacing unit portion 20, where it passes a capacitor 21 and a resistor 22 presenting matching of the level and setting the point of operation to the input signal at amplifier 23. In the feed-back loop at the amplifier there is a resistor 24 and a capacitor 25 with the purpose of supplying a time constant somewhat larger than 20 ms, corresponding, in the preferred embodiment, to pulses at 50 Hz. Additionally there is a semiconductor diode 26 to ensure that the negative pulses at the input of amplifier 23 do not exceed −0,7 V.

The signal from amplifier 23 is carried via an RC link 36, 27 to amplifier 28 having a high gain and acting as a comparator with a certain hysteresis; in other words a Schmitt trigger. Diodes 33 and 34 set forth the level of the output such that at output A it produces TTL level adjusted pulses between 0V and +5V.

From output A of the interfacing unit portion 20 the signal is carried to input A of the logic device 40. To simplify the description only a part of the logic device 40 has been demonstrated in detail in the schematic diagram. The signal is fed via a buffer 41 and into a monostable circuit created by logic circuits 42, 43, 44, 45, 49 and 50 which are parts of the larger logic device 40 of the special circuitry XC3030-44. From the internal input C a signal "high" is obtained by the monostable circuit, i.e. logic "one", during the period of time when the radiation hits any of the sensor elements 2, 3 and 4. When the radiation ceases and no more pulses trigger the monostable circuit in the logic device 40, when the output of OR gate 50 goes low, i.e. the negative edge, at the next clock pulse via point 55 into the D-type flip-flop circuit 51, a signal "high" will be produced and fed out via AND gate 52 to the internal output B as an indication that the detection of radiation has ceased.

Then the signals B and C are used in a conventional way to control the rest of the electronics of, for example, the CCD cell such that when signal C goes "high" it temporarily stops the clocking of the CCD cell which then starts to integrate its image elements to produce an X-ray imaging of e.g. a tooth. When signal B later goes "high" as an indication that the X-ray apparatus is deactivated, this signal B via the logic device 40 according to known technique starts the clocking of the CCD cell and the produced image is read out picture element by picture element and is fed to an ordinary graphic interfacing card in a standard personal computer (PC) according to the state of the art.

In a second preferred embodiment simultaneously the signal from the sensor elements is integrated, according to technique known by a person skilled in the art, to also obtain a measure of the dose detected by the sensor arrangement 2, 3, 4 or as previously discussed the CCD device itself. In this case this signal also controls at the same time the signal output B via a corresponding logic arrangement, such that when the stipulated X-ray dose for an appropriate exposure is received, the produced image from the image sensing member 5 is read out. Then in this alternative a complete exposure automatically is obtained still without having to make any connection between the imaging arrangement and the X-ray source if the X-ray source was adjusted such that its minimum activated time period at least corresponds to the minimum time period necessary to get a satisfactory exposure of an X-ray image on the image sensing member 5.

In a third preferred embodiment the signal B is taken out externally and is used to control the X-ray arrangement, whereby the X-ray arrangement immediately is deactivated when the integration sets forth that sufficient dose for the exposure is received. In this case an extra interfacing unit to the X-ray arrangement is needed, which is sensitive to the signal B and thus may control the external X-ray arrangement. This interfacing unit however is designed according to technique known by a person skilled in the art the construction of which does not fall within the scope of the present invention.

The arrangement according to the present invention may of course be constructed in a number of different ways by using different components than what has been indicated here without deviating from the spirit, object and scope of the invention which is defined by the attached claims.

I claim:

1. An X-ray imaging apparatus comprising:
    sensing means for generating electric signals in response to X-ray radiation;
    means for generating X-ray radiation towards said sensing means;
    interface means coupled to said sensing means for receiving said electric signals and generating a first interface signal when said sensing means detects X-ray radiation and generating a distinct second interface signal when said sensing means does not detect X-ray radiation; and
    means coupled to said interface means for displaying an image.

2. The apparatus of claim 1 wherein said sensing means comprises a sensing member for insertion into an oral cavity and having a front surface and an opposite rear surface, and at least two sensor elements positioned on said rear surface for generating said electric signals, said at least two sensor elements being spaced from each other.

3. The apparatus of claim 2 wherein said at least two sensor elements are detector diodes.

4. The apparatus of claim 2 wherein said interface means comprises a first circuit positioned on said rear surface for receiving said electric signals from said sensing means and generating an output signal.

5. The apparatus of claim 4 wherein said interface means comprises a second circuit for positioning outside of said oral cavity for receiving said output signal and generating said first interface signal and said second interface signal.

6. The apparatus of claim 1 wherein said sensing means is a CCD cell for insertion into an oral cavity and comprises a plurality of individual storage capacitors.

7. The apparatus of claim 6 wherein said interface means comprises a first circuit positioned on said CCD cell for receiving said electric signals from said CCD cell and generating an output signal.

8. The apparatus of claim 7 wherein said interfacing means comprises a second circuit for positioning outside said oral cavity for receiving said output signal and generating said first interface signal and said second interface signal.

9. A X-ray apparatus comprising:

sensing means for generating electric signals in response to X-ray radiation; and interface means coupled to said sensing means for receiving said electric signals and generating a first interface signal when said sensing means detects X-ray radiation and generating a distinct second interface signal when said sensing means does not detect X-ray radiation.

10. The sensing member of claim 9 wherein said sensing means comprises a sensing member for insertion into an oral cavity and having a front surface and an opposite rear surface, and at least two sensor elements positioned on said rear surface for generating said electric signals, said at least two sensor elements being spaced from each other.

11. The sensing member of claim 10 wherein said interface means comprises a first circuit positioned on said rear surface for receiving said electric signals and generating an output signal.

12. A method for imaging an object comprising the steps of:

(a) positioning a sensing member within an oral cavity in such a manner as to allow for positioning a tooth between said sensing member and an extra-oral source of X-ray radiation;

(b) generating X-ray radiation towards said tooth and said sensing member;

(c) generating electric signals from said sensing member in response to said X-ray radiation;

(d) generating a first control signal when said sensing member detects X-ray radiation and generating a distinct second control signal when said sensing member does not detect X-ray radiation;

(e) starting generation of an X-ray image at said sensing member by maintaining clocking signals to said sensing member in a static state in response to said first control signal; and (f) displaying an image of said tooth.

13. The method of claim 12 further including the steps of:

discontinuing maintaining said clocking signals in a static state and scanning said sensing member in response to said second control signal;

outputing image data resulting from said scanning step;

storing said image data; and displaying said image data.

14. The method of claim 12 further including the steps of:

verifying that said sensing member has been subjected to adequate X-ray radiation for imaging;

scanning said sensing member in response to said second control signal;

outputting image data resulting from scanning;

storing said image data; and displaying said image data.

* * * * *